United States Patent
Delgado et al.

(10) Patent No.: US 7,241,735 B2
(45) Date of Patent: Jul. 10, 2007

(54) PHARMACOLOGICALLY ACTIVE POLYPEPTIDE GLYCOCONJUGATES

(75) Inventors: Aurora Brieva Delgado, Madrid (ES); Vicente Garcia Villarrubia, Las Roza (ES); Antonio Guerrero Gomez-Pamo, Madrid (ES); Juan Pablo Pivel Raniert, Madrid (ES); Guillermo Gimenez Gallego, Madrid (ES); Jose Antonio Matji Tuduri, Madrid (ES)

(73) Assignee: Industrial Farmaceutica Cantabria, S.A., Santander (ES)

( * ) Notice: Subject to any disclaimer, the term of this patent is extended or adjusted under 35 U.S.C. 154(b) by 0 days.

(21) Appl. No.: 10/930,729

(22) Filed: Aug. 30, 2004

(65) Prior Publication Data

US 2005/0203004 A1   Sep. 15, 2005

Related U.S. Application Data

(62) Division of application No. 09/913,351, filed as application No. PCT/ES99/00338 on Oct. 21, 1999, now abandoned.

(30) Foreign Application Priority Data

Feb. 26, 1999   (ES)   ................................. 9900408

(51) Int. Cl.
 *A61K 47/48*   (2006.01)
 *C07K 14/415*   (2006.01)
(52) U.S. Cl. .................. 514/2; 514/12; 514/8; 514/23; 514/54; 530/300; 530/350; 530/370; 530/344; 530/395; 424/185.1; 424/193.1
(58) Field of Classification Search ................ 514/2, 514/12, 8, 23, 54; 530/300, 350, 370, 344, 530/395; 424/185.1, 193.1
See application file for complete search history.

(56) References Cited

U.S. PATENT DOCUMENTS 5,284,934 A   2/1994   Allen, Jr. ................... 530/370

FOREIGN PATENT DOCUMENTS

FR   2 691 465   11/1993

*Primary Examiner*—Chih-Min Kam
(74) *Attorney, Agent, or Firm*—Ladas & Parry LLP

(57) ABSTRACT

The invention relates to glycopeptidic glycoconjugates, in which the polysaccharide is obtained from *Candida utilis* cells and the peptides are obtained from *Ricinus communis* seeds. The glycoconjugates are used in the preparation of immunomodulating drugs that control the production of tumor necrosis factor (TNF).

4 Claims, 1 Drawing Sheet

SEQUENCE LISTING

```
<160> NUMBER OF SEQ ID NOS: 5

<210> SEQ ID NO 1
<211> LENGTH: 230
<212> TYPE: PRT
<213> ORGANISM: Artificial Sequence
<220> FEATURE:
<223> OTHER INFORMATION: Description of Artificial Sequence: Formula
      sequence
<220> FEATURE:
<221> NAME/KEY: MOD_RES
<222> LOCATION: (1)..(48)
<223> OTHER INFORMATION: Variable amino acid; this Xaa range may
      encompass 3-48 amino acids
<220> FEATURE:
<221> NAME/KEY: MOD_RES
<222> LOCATION: (50)..(62)
<223> OTHER INFORMATION: Variable amino acid; this Xaa range may
      encompass 9-13 amino acids
<220> FEATURE:
<221> NAME/KEY: MOD_RES
<222> LOCATION: (64)
<223> OTHER INFORMATION: Gln, Glu, Arg or Lys
<220> FEATURE:
<221> NAME/KEY: MOD_RES
<222> LOCATION: (65)
<223> OTHER INFORMATION: Variable amino acid
<220> FEATURE:
<221> NAME/KEY: MOD_RES
<222> LOCATION: (66)
<223> OTHER INFORMATION: Hydrophobic amino acid
<220> FEATURE:
<221> NAME/KEY: MOD_RES
<222> LOCATION: (67)
<223> OTHER INFORMATION: Leu, Ile, Val or Met
<220> FEATURE:
<221> NAME/KEY: MOD_RES
<222> LOCATION: (68)..(106)
<223> OTHER INFORMATION: Variable amino acid; this Xaa range may
      encompass 15-39 amino acids
<220> FEATURE:
<221> NAME/KEY: MOD_RES
<222> LOCATION: (109)
<223> OTHER INFORMATION: Hydrophilic amino acid
<220> FEATURE:
<221> NAME/KEY: MOD_RES
<222> LOCATION: (110)
<223> OTHER INFORMATION: Gln, Glu or His
<220> FEATURE:
<221> NAME/KEY: MOD_RES
<222> LOCATION: (111)
<223> OTHER INFORMATION: Leu or Val
<220> FEATURE:
<221> NAME/KEY: MOD_RES
<222> LOCATION: (112)..(117)
<223> OTHER INFORMATION: Variable amino acid
<220> FEATURE:
```

```
<221> NAME/KEY: MOD_RES
<222> LOCATION: (119)
<223> OTHER INFORMATION: Variable amino acid
<220> FEATURE:
<221> NAME/KEY: MOD_RES

```
            195                 200                 205
Xaa Xaa Xaa Xaa Xaa Xaa Xaa Xaa Cys Xaa Xaa Xaa Xaa Xaa
        210                 215                 220

Xaa Xaa Xaa Xaa Xaa Xaa
225             230

<210> SEQ ID NO 2
<211> LENGTH: 37
<212> TYPE: PRT
<213> ORGANISM: Ricinus communis

<400> SEQUENCE: 2

Glu Ser Lys Gly Glu Arg Glu Gly Ser Ser Gln Gln Cys Arg Gln
  1               5                  10                  15

Glu Val Gln Arg Lys Asp Leu Ser Ser Cys Glu Arg Tyr Leu Arg Gln
                 20                  25                  30

Ser Ser Ser Arg Arg
            35

<210> SEQ ID NO 3
<211> LENGTH: 68
<212> TYPE: PRT
<213> ORGANISM: Ricinus communis

<400> SEQUENCE: 3

Gln Gln Gln Glu Ser Gln Gln Leu Gln Gln Cys Cys Asn Gln Val Lys
  1               5                  10                  15

Gln Val Arg Asp Glu Cys Gln Cys Glu Ala Ile Lys Tyr Ile Ala Glu
                 20                  25                  30

Asp Gln Ile Gln Gln Gly Gln Leu His Gly Glu Glu Ser Glu Arg Val
            35                  40                  45

Ala Gln Arg Ala Gly Glu Ile Val Ser Ser Cys Gly Val Arg Cys Met
       50                  55                  60

Arg Gln Thr Arg
 65

<210> SEQ ID NO 4
<211> LENGTH: 34
<212> TYPE: PRT
<213> ORGANISM: Ricinus communis

<400> SEQUENCE: 4

Pro Ser Gln Gln Gly Cys Arg Gly Gln Ile Gln Glu Gln Gln Asn Leu
  1               5                  10                  15

Arg Gln Cys Gln Glu Tyr Ile Lys Gln Gln Val Ser Gly Gln Gly Pro
                 20                  25                  30

Arg Arg

<210> SEQ ID NO 5
<211> LENGTH: 65
<212> TYPE: PRT
<213> ORGANISM: Ricinus communis

<400> SEQUENCE: 5

Gln Glu Arg Ser Leu Arg Gly Cys Cys Asp His Leu Lys Gln Met Gln
  1               5                  10                  15

Ser Gln Cys Arg Cys Glu Gly Leu Arg Gln Ala Ile Glu Gln Gln Gln
                 20                  25                  30
```

```
Ser Gln Gly Gln Leu Gln Gly Gln Asp Val Phe Glu Ala Phe Arg Thr
        35                  40                  45

Ala Ala Asn Leu Pro Ser Met Cys Gly Val Ser Pro Thr Glu Cys Arg
    50                  55                  60

Phe
65
```

PHARMACOLOGICALLY ACTIVE POLYPEPTIDE GLYCOCONJUGATES

CROSS-REFERENCE TO RELATED APPLICATIONS

This patent application is a divisional application of U.S. patent application Ser. No. 09/913,351, filed on Aug. 13, 2001, now abandoned, which is a 371 of PCT/ES99/00338, filed on Oct. 21, 1999, which claims priority to Spanish Patent Application No. P9900408, filed on Feb. 26, 1999.

The growing awareness with regard to the mechanisms of function and regulation of the immunological system have raised, in the last years, the possibility of therapeutically modulating its function.

The great diversity of substances of different origin, natural and synthetic, capable of modulating some immunological mechanisms is due partly to the enormous possibility of recognizing substances which are foreign to the organism that is its own. In (G H Werner, P Follés "Immunostimulating agents: what next?. A review of their present and potential medical applications." Eur. J. Biochem 242, 1–19 (1996)) some of the products of recent development are described, as well as their possible therapeutical implications.

From among the various endogenous mediators there is one which raises one of the most important therapeutical challenges, it is the tumor necrosis factor (TNF). This molecule shows some special distinct characteristics (R Ksontini, S L D MacKay, L L Moldawer "Revisiting the role of tumor necrosis factor á and the response to surgical injury and inflammation" Arch. Surg. 133, 558–567 (1998). J L Alonso "La compleja fisiología del factor de necrosis tumoral." Inmunología 8, (3) 73–94 (1989). T. Calandra "Importance des cytokines dans les syndromes septiques." Med. Hyg. 49, 609–614 (1991). A Eigler, B. Sinha, G Hartman, S Endres "Taming TNF: strategies to restrain this pro inflammatory cytokines." Immunology Today 18, 487–492 (1997). R González-Amaro, C García-Monzón, L. García-Buey, R Moreno-Otero, J L Alonso, E Yagüe, J P Pivel, M López-Cabrera, E Fernández-Ruiz, F Sánchez-Madrid "Induction of Tumor Necrosis Factor á Production by Human Hepatocytes in Chronic Viral Hepatitis." J.Exp. Med 179, 841–848 (1994).):

The tumor necrosis factor (TNF) is a pleiotropic cytokine, given the great number of cells which respond to it. Normally produced by monocytes, it shows two active forms, one bonded to the membrane of the secreting cell, and another free one, derived from processing the former by a metaloproteinase, the converting enzyme of the tumor necrosis factor or TACE.

It is also documented the participation of other cells, other than monocytes, in the synthesis of TNFá, such as T lymphocytes, is documented. (A G Santis, M R Campanero, J L Alonso, F Sánchez-Madrid "Regulation of tumor necrosis factor (TNF)-á synthesis and TNF receptors expression in T lymphocytes through the CD2 activation pathway." Eur. J. Immunol. 22, 3155–3160 (1992). A G Santis, M R Campanero, J L Alonso, A Tugores, M A Alonso, E Yagüe, J P Pivel, F Sánchez-Madrid "Tumor necrosis factor-á production induced in T lymphocytes through the AIM/CD69 activation pathway." Eur. J. Immunol 22, 1253–1259 (1992).) and NK cells (I Melero, M A Balboa, J L Alonso, E Yagüe, J P Pivel, F Sánchez-Madrid, M Lopez-Botet "Signaling through the LFA-1 leucyte integrin actively regulates intercellular adhesion and tumor necrosis factor á production in natural killer cells." Eur. J. Immunol. 23, 1859–1865 (1993).).

There are some molecules which induce the production of TNF, such as the bacterial endotoxin or lipopolysaccharide (LPS), superantigens whose origin is bacterial, viral or from superior cells, and even other cytokines.

TNF, similarly to other cytokines, acts in a non-enzymatic manner, at concentrations in the nano to femtomole order, at the level of the secreting cell itself (autocrine activity), on adjacent cells (juxtacrine activity) as well as on neighboring tissues (paracrine activity) or distant ones (endocrine activity). This means that this molecule's activity, as well at that of other cytokines, is very much influenced by the "status" of the receptor cell and by its interaction, among others, with the excellular matrix.

Thus, in various situations, it has been found that the circulating TNF is not always the fundamental parameter, since although this one can be normal, there can also be very high local levels of this cytokine.

Two receptors have been described, in different cell types, named TNF receptors p55 (TNFR p55) and 75 (TNFR p75).

The interaction of these receptors with the free or bonded TNF gives way to an assorted spectrum of responses, which can be encompassed in three large groups: On the one hand, the activation of the inflammatory cascade, given the fact that TNF belongs to a group of proteins related to this one, among which are IL1, IL6, GM-CSF, etc. On the other hand, the activation of the cellular mediated response against the pathogenic aggression, specially by intracellular pathogens. And, on a third side, the apoptosis, or programmed cell death, specially evident in tumor cells. Nevertheless, in apoptotic response, TNF shows a dual response, since on the one hand, the activation by TNF of the NFkB transcription factor can protect some cell populations from death during an acute infection but, nevertheless, the hyperproduction of TNF can lead to death by apoptosis. As a consequence of the former, TNF is implicated in various pathologies. The relationship between its overproduction, local and/or systemic, and the outbreak and bad evolution of many pathological processes is extensively documented (R Ksontini, S L D MacKay, L L Moldawer "Revisiting the role of tumor necrosis factor á and the response to surgical injury and inflammation" Arch. Surg. 133, 558–567 (1998). J L Alonso "La compleja fisiología del factor de necrosis tumoral." Inmunología 8, (3) 73–94 (1989). T. Calandra "Importance des cytokines dans les syndromes septiques." Med. Hyg. 49, 609–614 (1991). A Eigler, B Sinha, G Hartman, S Endres "Taming TNF: strategies to restrain this pro inflammatory cytokines." Immunology Today 18, 487–492 (1997). R González-Amaro, C García-Monzón, L García-Buey, R Moreno-Otero, J L Alonso, E Yagüe, J P Pivel, M López-Cabrera, E Fernández-Ruiz, F Sánchez-Madrid "Induction of Tumor Necrosis Factor á Production by Human Hepatocytes in Chronic Viral Hepatitis." J. Exp. Med 179, 841–848 (1994).). The production of TNF by various cell types also contributes to the role this cytokine plays in the development of diverse pathological situations which include, for example, skin and gut lesions, associated to the host graft reaction (P F Piguet, G E Grau, B Allet, P Vassalli. "Tumor Necrosis Factor/Cachectin is an effector of skin and gut lesions of the acute phase of GRAFT-VS-HOST disease." J.Exp. Med. 166,1280–1289 (1987).), pneumocistosis (C E Reed. "Hypersensitivity pneumonitis and occupational lung disease from inhaled endotoxin." Immunology and Allergy Clinics of North America. 12 N° 4(1992)) or neurological pathologies (S W Barger "Tumor Necrosis Factor. The Good, the Bad and the Umbra." Neuroprotective Signal Transduction. Edited by M. P. Mattson Humana Press Inc. Totowa N.J.), pulmonary pathologies, chronic pathologies (such as intestinal inflammatory disease and rheumatoid arthritis) and sepsis. This cytokine also shows a very important role in two pathologies with a great incidence: asthma and cronic obstructive lung disease (P. Norman "Pulmonary diseases. Disease trends and market opportunities" Financial Times Pharmaceuticals Management Reports (1999)).

This background information brings up the difficulties in designing effective therapies based on the control of TNF in diverse pathological situations.

The design of new drugs requires establishing and elaborating experimental pharmacological models that reproduce the most important aspects of the pathology at issue. One of the most used models in the search for drugs capable of controlling the production of TNF is the murine model of systemic induction of TNF by bacterial endotoxine (LPS). Other widely used models are those in which the in vitro stimulation of cells belonging to the granulocytomacrophage lineage for the production of the said cytokine are studied.

One of the most outstanding aspects, from the scientific point of view, is the great chemical diversity of products which are accorded the capacity to control TNF hyperproduction in various in vivo and in vitro experimental models. Among these, can be mentioned, antioxidants (N Satomi, A Sakurai, R Haranaka, K Haranaka "Preventive Effects of Several Chemicals Against Lethality of Recombinant Human Tumor Necrosis Factor." Journal of Biological Response Modifiers. 7, 54–64 (1988).), cannabioids (R Gallily, A Yamin, Y Waksmann, H Ovadia, J Weidenfeld, A Bar-Joseph, A Biegon, R Mechoulanm, E Shohami. "Protection against Septic Shock and Suppression of Tumor Necrosis factor á and Nitric Oxide Production by Dexanabinol (HU-211), a Nonpshychotropic Cannabinoid." The Journal of Pharmacol. and Experimental Therapeut. 283, 918–924 (1997).), IL10 (S R Smith, C Terminelli, G Denhardt, S Narula, G Jeanette Thorbecke "Administration of Interleukin-10 and the Time of Priming Protects *Corynebacterium parvum*-Primed Mice against LPS- and TNF-a-induced Lethality." Cellular Immunology 173, 207–214 (1996).), Thalidomide (AL Moreira, J Wang, E N Sarno, G Kaplan. "Thalidomide protects mice against LPS-induced shock." Brazilian Journal of Medical and Biological Research 30: 1199–1207 (1997). S M McHugh, T L Rowland "Thalidomide and derivatives: immunological investigations of tumour necrosis factor-alpha (TNF-á) inhibition suggest drugs capable of selective gene regulation." Clin Exp. Immunol 110: 151–154 (1997). J D Klausner, V H Freedman, G Kaplan "Thalidomide as an Anti-TNF-á Inhibitor: Implications for Clinical Use." Clinical Immunology and Immunopathology. 81, 219–223 (1996).), Chlorpromacine (M. Gadina, R. Bertini, M. Mengozzi, M. Zandalasini, A. Mantovani and P. Ghezzi. "Protective Effect of Chlorpromazine on Endotoxin Toxicity and TNF Production in Glucocorticoid-Sensitive and Glucocorticoid-Resistant Models of Endotoxic Shock." J.Exp. Med. 273, 1305–1310 (1991).), Benzydamine (A. Gluglielmotti, L. Aquilini, M. T. Rosignoli, C, Landolfi, L. Soldo, I. Coletta and M. Pinza "Benzydamine protection in a mouse model of endotoxemia." Inflamm. Resp. 46, 332–335 (1997).), hydrazine-sulphate (R. Silverstein, B. R. Turley, C. A. Christoffersen, D. C. Johnson and D. C. Morrison "Hydrazine Sulfate Protects D-Galactosamine-sensitized Mice against Endotoxin and Tumor Necrosis factor/Cachectin Lethality: Evidence of a Role for the Pituitary." J.Exp. Med. 173, 357–365 (1991).) and natural extracts (H. Ueda and M. Yanazaki "Inhibition of Tumor Necrosis Factor á Production by Orally Administering a Perilla Leaf Extract." Biosci. Biotech. Biochem. 61, 1292–1295 (1997).).

Likewise, in the study of clinical situations in patients with pathologies in which it is known that TNF plays a role in relation to its evolution, the effect of the various active principles in the regulation of TNF production, in vitro, on behalf of isolated monocytes of peripheric blood, has been studied. Among them, we can mention ciplofloxacin (S Bailly, M Fay, B Ferrua, M A Gougerot-Pocidalo "Ciprofloxacin treatment in vivo increases the ex vivo capacity of lipopolysaccharide-stimulated human monocytes to produce IL-1, IL-6 and tumour necrosis factor-alpha." Clin. Exp. Immunol. 85, 331–334 (1991).), rolipram (J Semmler, H Wachtel, S Endres "The specific type IV phosphodiesterase inhibitor rolipram suppresses Tumor Necrosis Factor-á production by human mononuclear cells." Int. J. Immunopharmac. 15, 409–413 (1993).), vesnarinone (T Kambayashi, N Mazurek, ChO Jacob, N Wei, M Fong and G Strassmann. "Vesnarinone as a selective inhibitor of Macrophage TNF-á release." Int J. Immunnopharmac, 18, 371–378 (1996).), prostacyclin analogues (A Jörres, H Dinter, N Topley, G M Gahl, U Frei, P Scholz "Inhibition of Tumour Necrosis Factor production in endotoxin-stimulated human mononuclear leukocytes by the prostacyclin analogue iloprost: Cellular Mechanisms." Cytokine 9, 119–125 (1997).), pentoxifylline (B J Dezube, M L Sherman, J L Fridovich-Keil, J Allen-T Ryan, A B Pardee. "Down-regulation of tumor necrosis factor expresion by pentoxifylline in cancer patients: a pilot study." Cancer Immunol Immunother 36: 57–60 (1993).). A special case is the mention of corticoids in terms of its known relation with inhibition of the TNF gene (S Abe, T Yamamoto, S Iihara, M Yamazaki, D Minuzo. "A possible role of glucocorticoids: an intrinsic inhibitor of the cytotoxic activity of Tumor Necrosis Factor." Jpn. J, Cancer Res. (Gann) 79: 305–308 (1988). J Han, P Thompson, B Beutler "Dexamethasone and Pentoxifylline Inhibit Endotoxin-induced Cachectin/Tumor Necrosis Factor Synthesis at Separate Points in the Signaling Pathway." J. Exp. Med. 172, 391–394 (1990). I M H Debets, T J M Ruers, M P M H Van Der Linden, C J Van den Linder, W A Buurman. "Inhibitory effect of corticosteroids on the secretion of tumor necrosis factor (TNF) by monocytes is dependent on the stimulus inducing TNF synthesis." Clin. Exp. Immunol. 78: 224–229 (1989).). It is worth mentioning that the modulation of cytokine levels is already being mentioned as a specific "target" in the design of new drugs (K Cooper, H Masamune "Cytokine Modulation as a Medicinal Chemistry Target." Annual Reports in Medicinal Chemistry-27, Chapter 22). Other attempts to control the effects of this cytokine, in situations of sepsis as well as ulcerative colitis and rheumatoid arthritis, is related to the development of monoclonal anti-TNF antibodies (A Trilla, P Alonso "Anti-cuerpos monoclonales en el tratamiento del shock séptico." Med. Clin. 99: 778–780 (1992). J G Sinkovics "Monoclonal antibodies in the treatment of endotoxin shock" Acta Microbiologica Hungarica 37: (1990). S B Porter "Current Status of Clinical Trials With Anti-TNF" Chest 112: 6 (1997). J R O'Dell "Anticytokine therapy. A new era in the treatment of rheumatoid arthritis" New Eng. J. Med. 340, 310–312 (1999). R A van Hogenzand, H W Verpaget "The future role of anti-tumor necrosis factor a products in the treatment of Crohn's disease" Drugs 56, 299–305 (1998). F Mackay, J L Browning, P Lawton, S A Shah, M Comiskey, A K Bhan, E Mizoguchi, C Terhorst, S J Simpson "Both the lymphotoxin and tumor necrosis factor pathways are involved in experimental murine models of colitis "Gaestroenterology 115, 1464–1475 (1998)). Nevertheless, and despite the extensive knowledge about this cytokine, including its molecular biology, this has not allowed the development of safe and effective therapeutic agents in the control of its hyperproduction.

A critical analysis of all these possible therapeutical options indicates that, for example in the case of the monoclonal anti TNF, these have not been effective in the case of acute pathologies and show a great variability in their affinity to cytokine, although lately some successful cases have been reported in the case of rheumatoid arthritis and ulcerative colotis (J R O'Dell "Anticytokine therapy. A new era in the treatment of rheumatoid arthritis" New Eng. J. Med. 340, 310–312 (1999). R A van Hogenzand, H W Verspaget "The future role of anti-tumor necrosis factor á products in the treatment of Crohn's disease" Drugs 56, 299–305 (1998).); other products show a very strong toxicity profile, as in the case of Thalidomide, or show a main activity that makes them difficult to handle such as ciprofloxacin or Rolipram. In other cases there is a lack of chemical definition, and therefore of reproducibility from batch to batch, as with extracts. Finally, in the case of corticoids, inhibitors of the TNF gene expression, they show an important group of contraindications.

The knowledge of the functional mechanisms of the immune system has allowed in the past few years the development of substances known as immunomodulators. There are pathological situations in which resourcing to immunomodulators becomes specially important, such as in autoimmune diseases, with the corresponding imbalance of the immune system, iatrogenic immunosuppression (such as that occurring in transplants, antineoplastic therapy or specially traumatic surgery) or environmental (caused by stress or pollution). On the other hand, nowadays, many therapeutical protocols include immunomodulators as coadjuvants to the specific antioncogenic or antiinfective therapy (E Garaci, F Pica, G Rasi, A T Palamara, C Favalli "Combination therapy with BRMs in cancer and infectious diseases" Mechanisms of Ageing and Development 96, 103–116 (1997).

An important group within immunomodulators are those designed with the objective of stimulating natural immunity mechanisms, particularly the NK activity or the phagocytic and microbicide activities of the mononuclear phagocytic system. Among these, could be mentioned, bacterial extracts, BCG, *Corynebacterium parvum*, muramildipeptide derivates, as well as polysaccharides, specially glucans extracted from yeast (A Aszalos "Immunstimulators of microbial origin" in "Antitumor compounds of natural origin" CRC Press (1982)). Although the previously described molecules have shown their effectiveness as activators of the monocyte-macrophage system, as well as a certain efficacy as antitumor compounds, their administration implies two undesirable side effects: On the one hand they block the hepatic metabolization systems—a property which they share with other immunomodulatory substances and which hinders coadjuvant administration with other therapies, such as antibiotics or cytostatics, and on the other hand, and very specially, they become sensitive to bacterial endotoxin, and it might be the case that the endotoxin released by the antibiotic action is more toxic for the patient in the presence of the immunologic coadjuvant (M Trautmann, R Zick, T Rukavina, A S Cross, R Marre "Antibiotic-induced release of endotoxin: In vitro comparison of meropenem and other antibiotics" J. Antimicr. Chemother. 41, 163–169 (1998)).

The aforementioned infers, therefore, there is a narrow therapeutical window which consists of finding products capable of selectively inhibiting some TNF actions without blocking, or even more stimulating, the natural immunity response.

Within the types of molecules whose use has been more controversial are the peptide type immunomodulators. The controversy is based on the fact that although this type of molecules show very promising activities, such as specific interaction with receptors, specific inhibition of other proteins—like the protease inhibitors—etc, they show problems of bioavailability, specially by oral route, sensitivity to proteases, short half-life and causing allergic or anaphylactic reactions. A very recent review of peptides and proteins as immunomodulators emphasize these characteristics (J E Talmadge "Pharmacodynamic aspects of peptide administration biological response modifiers" Advanced Drug Delivery Reviews 33, 241–252 (1998)): "Various paradigms distinguish the therapeutic activity of proteins in comparison with the classic drugs of low molecular weight. These differences are predominantly associated with the pharmacodynamic attributes of proteins. So, this is critical to understand the pharmacology of these drugs as well as to optimize their therapeutic activity, or more generally, to identify it. These paradigms include:

The short half-life of proteins and the need for subcutaneous or continuous infusion administration in order to obtain the maximum activity.

The apparent "bell-shape" response.

The need of a chronic administration associated with the perceived mechanism of action of said molecules.

The optimum activity of said agents as coadjuvant therapy administered together with chemo and/or radiotherapy, and that The maximum coadjuvant immunotherapeutic activity is found in patients with minimum residual illness."

The object of the present invention is the fact that certain peptides or proteins, with special physico-chemical characteristics defined by precise structural requirements, are capable of forming non-covalent conjugates with specific molecules of polysaccharide nature, defined by such structural characteristics that make the formation of these conjugates possible, and that these conjugates show activity by oral route in the modulation of the human or animal immune response. This modulation is translated into the downward regulation of the TNF production induced in certain experimental conditions, being also capable of stimulating the mononuclear—phagocytic system, of expanding the granulocyte-macrophage compartment and not showing inhibition of the hepatic metabolization systems.

It is necessary to emphasize two points which make specially important the object of the present invention:

The first one is that the non-covalent conjugates formed are active by oral route, therefore representing a novelty in the field of peptides biologically active by this route, and overcoming the drawbacks in an original manner for this route of administration. These drawbacks are perfectly described in the following papers: B L Ferraiolo, L Z Benet "Peptides and proteins as drugs" Pharmaceutical Research 4, 151–194 (1985); F M Rollwagen, S Baqar "Oral cytokine administration" Immunol. Today 17, 548–550 (1996); Solis-Pereyra, N Aattouri, D Lemonnier "Role of food in the stimulation of cytokine production" Am. J. Clin. Nutr. 66, 521S–525S (1997); A Fasano "Innovative strategies for the oral delivery of drugs and peptides" Trends in Biotech. 16, 152–157 (1998); G M Pauletti, S Gangwar, T J Siahaan, J Aubé, R T Borchardt "Improvement of oral peptide bioavailability: Peptidomimetics and prodrug strategies" Adv. Drug Deliv. Rev. 27, 235–256 (1997); J J Hols, C Deacon, M B Toft-Nielsen, L Bjerre-Knudsen "On the treatment of diabetes mellitus with Glucagon-like peptide-1" Ann. New York Acad. Sci. 865, 336–343 (1998)). In this sense, it should be pointed out that this is not the only example of protein activity by oral route (Y Nagao, K Yamashiro, N Hara, Y Horisawa, K Kato, A Uemera "Oral administration of IFN-á potentiates immune response in mice" J Interferon and Cytokine Res. 18, 661–666 (1998); S Kaminogawa "Food allergy, oral tolerance and immunomodulation. Their molecular and cellular mechanisms" Biosci. Biotec. Biochem. 60, 1749–1756 (19961; H Uwata, T-T Yip, K Yamauchi, S Teraguchi, H Hayasawa, M Tomita, T. W. Hutchens "The survival of ingested lactoferrin in the gastrointestinal tract of adult mice" Biochem. J. 334, 321–223 (1998); J Xu-Amano, W K Aicher, T Taguchi, H Kiyono, J R McGhee "Selective induction of Th2 cells in murine Peyer's patches by oral immunization" Internat. Immunol. 4, 433–445 (1992)).

The second one is that there are described polysaccharide-protein complexes, covalent as well as non-covalent, with biological activity but that, contrary to the object of the present invention, they are in general associations in which the addition of certain peptides produce an increase in the antigenic response of weakly immunogenic polysaccharides achieving, thanks to the association, a T dependent response against a polyssacharide antigen that is only T independent and of low response. (H-K Guttormsen, L M Wetzler, R W Finberg, D L Kasper "Immunologic memory induced by a glycoconjugate vaccine in a murine adoptive lymphocyte transfer model" Infection and Immunity 66, 2026–2032 (1998); M A Avanzini, A M Carrè, R Macario, M. Zecca, G Zecca, A Pession, P Comoli, M Bozzola, A Prete, R Esposito, F Bonetti, F Locatelli "Immunization with *Haemophilus influenzae* type b conjugate vaccine in children given bone marrow transplantation: Comparison with healthy age-matched controls" J. Clin. Immunol. 18, 193–301 (1998); E F E Babiker, A Hiroyuki, N Matsudomi, H Iwata, T Ogawa, N Bando, A Kato "Effect of polysaccharide conjugation or transglutaminase treatment on the allergenecity and functional properties of soy protein" J. Agric. Food Chem. 46, 866–871 (1998)). It should be pointed out that, unlike the present invention, in those cases in which polysaccharide-protein associations with immunomodulatory activity have been described, these associations are covalent and come from the same natural source (K Noda, N Ohno, K Tanaka, M Okuda, T Yadomae, K Nomoto, T Shoyama "A new type of biological response modifier from *Chlorella vulgaris* which needs protein moiety to show antitumor activity" Phytotherapy Res. 12, 309–319 (1998); D Sabolovic, L Galoppin "Effect of a protein bound polysaccharide (PS-K on tumor development and infections in splenectomized rats and mice" Int. J. Immunopharmac. 8, 41–46 (1986)).

To provide a better understanding of the characteristics of the invention, a detailed description follows.

Figure 1:
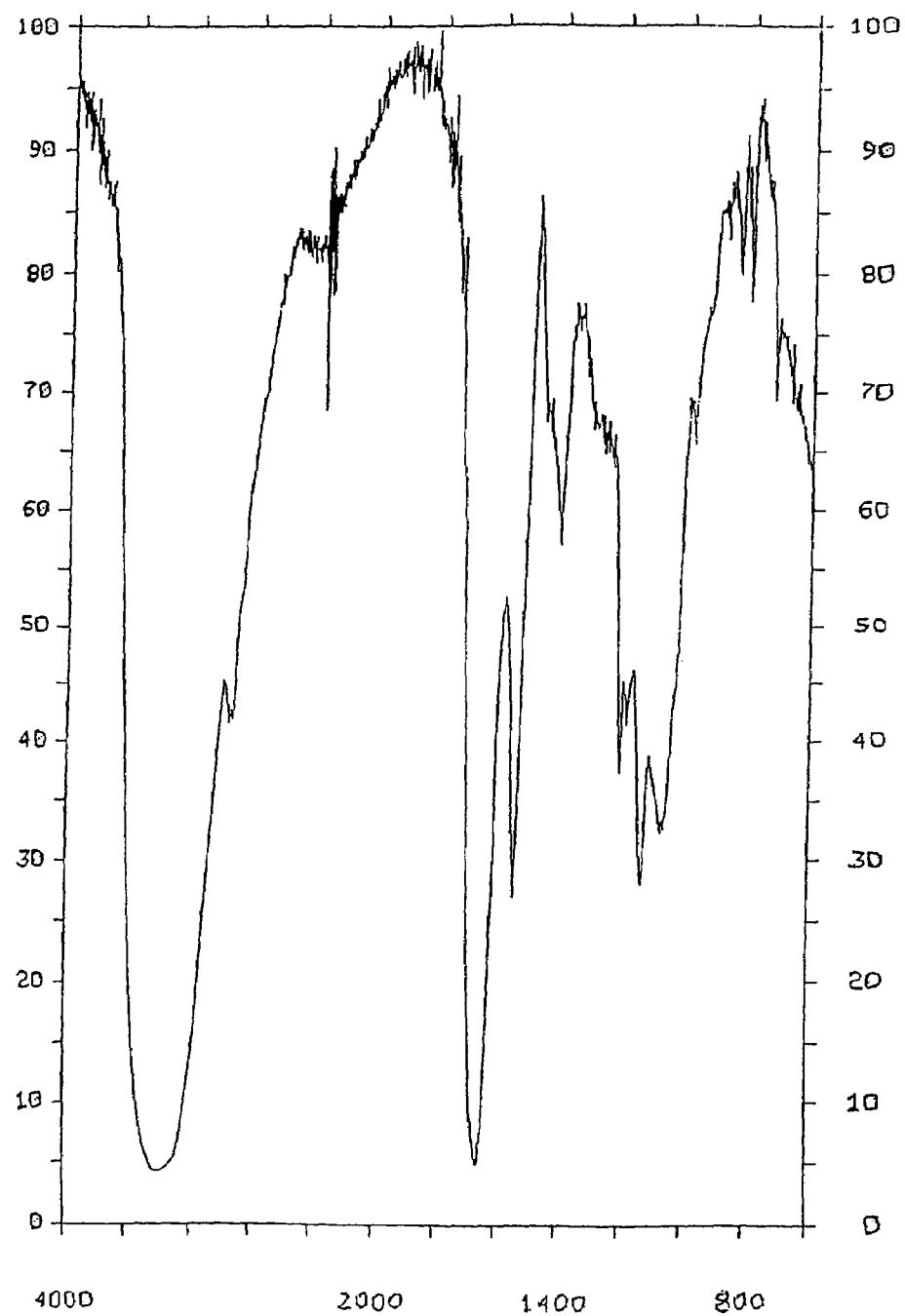
FIG. 1 shows an example of the infrared spectrum of the glycoconjugate.

This invention describes the formation and pharmacological properties of conjugates of substantially pure specific polypeptides and specific polysaccharides, for the manufacture of therapeutical compositions for the treatment of immunological disfunctions, infections and/or tumors.

These conjugates are pharmacologically active, while none of their components (polypeptide or polysaccharide) show the pharmacological activities of the conjugates. Likewise, these conjugates show different stoichiometries in the polysaccharide polypeptide relation, being the pharmacological activities dependent on these stoichiometries.

The technical description of the present invention is composed of the following parts: a) requirements that the molecules of polysaccharide nature object of the present invention must comply with; b) requirements that the molecules of polypeptide nature object of the present invention must comply with; c) consequences of these requirements: formation of the polysaccharide polypeptide conjugates; d) biological activities of the polysaccharide-polypeptide conjugates.

A) Requirements that the Molecules of Polysaccharide Nature Object of the Present Invention Must Comply with.

Molecules of polysaccharide nature object of the present invention must comply with the following requirements:

Their origin must be microbial, not viral, and in particular originated in walls of yeast. Their average molecular weight must be situated between 50 and 250 Kda; these polysaccharides must be soluble in water or in saline media with ionic strength similar to that produced by sodium chloride solutions at concentrations between 0 and 250 mM, being soluble under these conditions at least at 0.1 mg/mL. In solutions in neutral media they must show negative charge, mainly due to phosphate groups that confer a special reactivity against ää T cells (A Salerno, F Dieli "Role of ää T lymphocytes in immune response in humans and mice" Critical Rev. Immunol 18, 327–357 (1998)), with a relation of phosphate residues by monosaccharide between 1 to 5 and 1 to 25; they must not show neither sulphate nor carboxylate groups. With regard to their composition of monosaccharides, mannose must be the main one (at least 40%), being the others glucose and/or galactose; the content of nitrogen monosaccharides must not surpass 5% of the total. The main skeleton must be formed by 1–6 bonds, preferably with 1–2 branches, and in a way that the monosaccharides in the branches do not overpass 60%. They must not show associated lipid groups.

With regard to their physico-chemical behaviour, they must show domains capable of interacting with octadecyl-silane in aqueous media and must not gelify in aqueous or saline media, specially in the presence of calcium at concentrations below or equal to 2 mM. They must be capable of forming conjugates with polypeptides or peptides with the characteristics described in the following section, and those conjugates must be stable under physiological conditions.

They must show no anticoagulant activity. They must be capable of enduring the physico-chemical and enzymatic conditions of the gastrointestinal tract, thus guaranteeing the activity of the conjugates by oral route; this activity is originated through the interaction of the conjugate with the intestinal lymphatic tissue and the generation of a systemic response through the ää T cells bridge (A K Abbas, A H Lichtman, J S Pober "Cellular and molecular immunology" W. B. Saunders Co. Philadelphia, pp 232–236 (1994). T W Mak, D A Ferrick "The ää T-cell bridge: Linkage innate and adquired immunity" Nature Med. 4, 764–765 (1998)), bridge that shows a special decline in old age (G Pawelec, R Solana, E Remarque, E Mariani "Impact of aging on innate immunity" J. Leuk. Biol. 64, 703–712 (1998)).

B) Requirements that the Molecules of Polypeptide Nature Object of the Present Invention Must Comply with:

The molecules of polypeptide nature object of the present invention must comply with the following paradigms:

They must be capable of resisting the physico-chemical and enzymatic conditions of the gastrointestinal tract, thus guaranteeing the activity of the conjugates by oral route.

They must be capable of forming conjugates with polysaccharides with the characteristics described in the previous section, and these conjugates must be stable under physiological conditions.

Those polypeptides stabilized through the disulphur bridges or alternatively stabilized through chemical manipulations which lead to the formation of dimethylene bridges are considered to be of particular interest.

This type of structures represent at the same time the stereospecificity characteristic of polypeptides with the chemical stability characteristic of drugs of low molecular weight.

Possible sources of this type of molecules are vegetable seed reservoir polypeptides, vegetable defensive polypeptydes, vegetable sweetener polypeptides, etc.

In order to do this, they must comply with the following requirements:

Molecular weight: Between 4 and 30 KDa.

Solubility: soluble in water or in saline media, with ionic strength similar to that produced by solutions of sodium chloride between 0 and 0.25 M, at concentrations equal or higher than 0.1 mg/ml.

In their native conditions they must be resistant to trypsin type proteases, chemotrypsin and/or pepsine, in the optimal working conditions of these enzymes; in their native condition they must be resistant to an acid pH (in similar conditions to those of the stomach), for a period of time no less than 1 hour.

They must be capable of resisting the physico-chemical and enzymatic conditions of the gastrointestinal tract, thus guaranteeing the activity of the conjugates by oral route; this activity is originated through the interaction of the conjugate with the intestinal lymphatic tissue and the generation of a systemic response through the ää T cells bridge (A K Abbas, A H Lichtman, J S Pober "Cellular and molecular immunology" W. B. Saunders Co. Philadelphia, pp 232–236 (1994). T W Mak, D A Ferrick "The ää T-cell bridge: Linkage innate and adquired immunity" Nature Med. 4, 764–765 (1998)), bridge that shows a special decline in old age (G Pawelec, R Solana, E Remarque, E Mariani "Impact of aging on innate immunity" J. Leuk. Biol. 64, 703–712 (1998)).

When they are denaturated by agents such as 8 M guanidine chloride or 6 M urea and in the presence of the reducing-agents of the disulphur bridges, such as dithiothreitol or ã mercaptoethanol at concentrations of 6.4 mM, they must be capable of recovering their native condition, evaluated starting from the spectra of circular dichroism in the range of 280–200 nm, by simple dilution of the denaturating agents.

Preferably non glycosilates.

Stabilized by disulphur or dimethylene bridges, they can be oligomeric, specially dimeric, and in this case they must have at least two disulphur or dimethylene intercatenary bridges.

Sequence: In order to comply with the above conditions, the polypeptides object of the present invention must include in their sequence the following consensus sequence (SEQ ID NO: 1): $Z_{3-48} CZ_{9-13}$ C (Q, E, R, K) Z ($Z_{hydrophobic}$) (LIVM) $Z_{15-39}$ CC ($Z_{hydrophilic}$) (Q,E,H) (L,V) $Z_6$ CZC $Z_2$ (L,I) $Z_{13-56}$ G $Z_{15-26}$ CZ (V,I,L,M) $Z_{1-8}$ $CZ_{1-12}$ (( ) Indicates 1 amino acid, being within the parenthesis the possible ones in order of preference. $Z_n$ indicates n amino acids whichever they are. This sequence has $CZ_nC$ domains (Tamaoki et al "Folding motifs induced and stabilized by distinct cystine frameworks" Protein engineering 11, 649–659 (1998)).

In the case of dimeric polypeptides, the consensus sequence could be distributed between the sequences of the two subunits, which implies the existence of a point of hydrolysis which must be in one of the zones indicated by $Z_n$ of this sequence.

They must have a significant proliferous effect on the model of murine splenocytes (proliferation value 3 with respect to control). The effect of the in vitro treatment with polypeptides on splenic cells of mice Balb/c is evaluated. The assay is carried out in microplate and the proliferation is quantified by a colorimetric method (T Mosmann "Rapid colorimetric assay for cellular growth and survival: Application to proliferation and cytoxicity assays" J. Immunol. Methods 65, 55–63 (1983).

C) Formation of Polysaccharide Polypeptide Conjugates:

The formation of polysaccharide polypeptide conjugates is an spontaneous phenomenon at room temperature starting from solutions of both components in water or saline solutions whose ionic strength does not exceed the equivalent of that of a solution of 0.15 M sodium chloride. The polysaccharide polypeptide conjugates can be within the 1/1 to 1/19 mol/mol range. The conjugates are formed by mixing at temperatures between 15 and 40° C. and shaking gently, between 1 and 100 rpm, solutions of the polypeptide and the polysaccharide that contain the desired amount of each one of them (so that they comply with the indicated mol/mol relations) and in the indicated media. The mixture of the solutions is maintained under shaking, for a length of time between 5 and 60 minutes. Once the conjugate is formed, it can be administered as is or in any adequate galenical form, prior sterilizing filtration, in the case of its use by parenteral, intramuscular or subcutaneous route.

It is also possible to form conjugates between a polysaccharide and two polypeptides, as long as they maintain the above indicated polysaccharide/total polypeptides ratios, and they comply, apart from the above indicated conditions, with the following conditions:

a) The mol/mol ratio between the two polypeptides is between 1/3 and 3/1.

b) The two polypeptides are of the same biological origin.

c) The two polypeptides show a sequence homology of no less than 25% (and that the sum of the strict homology and allowed replacements are not less than 50%).

D) Galenic Forms

Injectable pharmaceutical form: The conjugate is dialyzed or diafiltered against an apirogenous sterile saline solution and is sterilized by filtration by 0.22 ì in apyrogenic sterile conditions.

Oral forms: The conjugate can be administered in a solution as obtained or starting from an extemporaneous solution of the conjugate lyophilized in water, and also in any conventional pharmaceutical galenic form, such as tablets, pills, or capsules, syrups or any liquid pharmaceutical form for oral use, employing the necessary excipients.

Topical pharmaceutical forms: The conjugate can be formulated in topical preparations at concentrations between 1 and 5% (w/w) in conventional forms such as gel, cream, ointments, using the common pharmaceutical excipients.

EXAMPLE 1

1. Obtaining the Polysaccharide

It is obtained, for example, based on the process described in G Kogan, J Sandula, V Simkovicova "Glucomannan from *Candida utilis*. Structural investigation" Folia Microbiol (Praha) 38, 219–224 (1993). K H Rademacher, Y Koch "(Structure of the cell wall mannans of synchronously multiplying *Candida utilis* cells)" Z All. Microbio 19, 65–67 (1979)), in the following way:

In this example, the polysaccharide, an integral part of the conjugate object of the present invention, is obtained starting from commercial desiccated *Candida utilis* for human use, by the process described below:

1.1 Weight approximately 100 g of soy seeds. Soak them for 24 hrs in water.
1.2 Wash the seeds several times.
1.3 Grind them in a mortar or a mincer.
1.4 Prepare an aqueous solution of 2 l containing 6.25 g/l of $MnSO_4.H_2O$ and 3.33 g/l of $CoCl_2.6H_2O$. Temper at 37° C. Add, stirring in a magnetic stirrer, 0.21 g/l of $MnO_2$, 62.5 g/l of desiccated *C. utilis* and 12.5 g/l of the seed milling.
1.5 Incubate in orbital stirrer at 37° C. and 200 rpm for 48 hours.
1.6 Allow to stand, separate the supernatant and centrifuge at 2300× g 10 minutes at room temperature. Filter the centrifuge supernatant with paper to vacuum and by filter to 0.45 ì.
1.7 Dialyze against 5 times its volume in water MilliRO, for one day at 4–8° C., changing the water between 3 to 5 times.
1.8 If any precipitate appears, centrifuge it at 2300× g during 10 minutes at room temperature in order to eliminate it.
1.9 Lyophilize, if desired, the dialyzate or the centrifuged dialyzate.
1.10 Purify by traditional methods, such as molecular permeation chromatography (in gel such as Sephacryl S-200 or S-400 or similar), ultrafiltration (through molecular cut membrane 50.000 of Amicon or similar) etc.
1.11 It can be lyophilized if so desired.
1.12 By means of this process a pure product is obtained in quantities ranging from 0.2 and 6.4 g polysaccharide/100 g yeast, which allows for its industrial scaling.

The polysaccharid thus obtained has an average molecular weight of 150 KDa±30 KDa determined by high performance liquid chromatography of molecular exclusion in a TSK40 column, using a 10 mM phosphate buffer, 0.3 M NaCl, pH 7.4 as an eluent and detection by refraction index, comparing with Fluka dextran standards as molecular weight standards. It shows a phosphate contents of 1 phosphate residue per each 15 monosaccharide residues, determined according to the Method of Hess and Deer (H H Hess, J E Deer "Assay of inorganic and organic phosphorous in the 0.1–5 nanomolrange." Anal Biochem 63:607–613 (1975)). Its composition in monosaccharides is determined by hydrolysis, reduction, acetylation and gas chromatography of alditol acetylated derivates (according to the methods described in A Novotny "Basic exercises in Immunochemistry" S. Verlag Ed. Berlin, Heildelberg, New York pp 127–131 (1979); G Keleti, W H Lederer "Handbook of Micromethods for the Biological Science" Ed. Van Nostrand Reinhold. New York. pp 55–57 and H P Burchfield, E E Storrs "Biochemical Applications of Gas Chromatography" Academic Press. New York (1962)) is mannose 84±6%, glucose 7±3% and galactose 1±1%. The structural analysis determined by degradation of Smith (F Smith, R Montgomery Meth Biochem Anal 3:153 (1956)) demonstrated that said polysaccharide presents a lineal skeleton 1–6, in which can be found 45±5% of monosaccharides, with branches 1–2, in which can be found 45±5% of monosaccharides. It gives no positive reactions to carboxylate or sulphate. The polysaccharide thus obtained interacts with octadecylsilane when injected into a column of these characteristics in an aqueous media (column C18 Vydac), requiring a concentration of at least 25% of acetonitrile for elution. The polysaccharide thus obtained does not modify neither its chromatographic behaviour in the TSK 40 column previously mentioned nor its phosphate contents after a 1 hour incubation in incomplete gastric juice (2 g/l NaCl, 7 ml/l concentrated hydrochloric acid) at 37° C., shaking at 50–100 rpm. The polysaccharide thus obtained does not gelify in the presence of calcium chloride at concentrations below 10 mM. The polysaccharide thus obtained does not show any anticoagulant in vitro activity (T A Harper "Laboratory guide to disordered haemostasis" pp 76–77 Butterworths (1970)).

2. Obtaining the Polypeptide

It is obtained, for example, based on the process described by F S Sharief, S S L Li "Aminoacid sequence of small and large subunits protein from *Ricinus communis*" J. Biol. Chem. 257, 14753–14759 (1982); J Godinho da Silva Jr, O L T Machado, C Izumi, J C Padovan, B T Chait, U A Mirzaa, L J Geene "Aminoacid sequence of a new 2S albumin which is part of a 29-kDa precursor protein" Arch. Biochem. Biophys. 336, 10–18 (1996); G M Neumann, R Condron, G M Polya "Purification and sequencing of napin-like protein small and large subunits from *Momordica charantia* and *Ricinus communis* seeds and determination of sites phosphorylated by plant $Ca^{2+}$—dependent protein kinase" Biochem. Biophys. Acta 1298, 223–240 (1996); M E H Bashir, I Hubatsch, H P Leinenbach, M Zeppezauer, R C Panzani, I H Hussein "Ric c1 and Ric c3, the allergenic 2S albumin storage proteins of *Ricinus communis*: Complete primary structures and phylogenetic relationships" Int. Arch. Allergy Immunol. 115, 73–82 (1998) in the following way:

In this example, the polypeptide, an integral part of the conjugate object of the present invention, is obtained starting from non-germinated seeds of *Ricinus communis*, by the method described below:

2.1 Grind 100 g of whole seeds, previously washed in water, until a non compact paste is obtained.

2.2 The obtention of the extract is carried out by magnetic stirring the paste with 500 ml of water for 18 hours at 4° C.

2.3 Next, eliminate the residue of the seeds by successive filtration through a stainless steel filter mesh of 0.2 mm light, Hyflo supercell coating, and by prefilter of polypropylene and filters of nitrocellulose or similar with 40 mm diameter and light of 80 ìm, 8 ìm, 5 ìm, 0.45 ìm and 0.22 ìm 2.4 The filtrate is acidified to pH 1.5 with phosphoric acid diluted with water MilliQ at 50% (v/v).

2.5 Heat it at 56° C. in a water-bath with thermostat for 120 minutes with gentle magnetic stirring.

2.6 Centrifuge at 2300×g for 15 minutes at room temperature. Separate carefully the supernatant so that it does not get contaminated with the precipitate.

2.7 Neutralize the supernatant with a solution of NaOH at 20% (w/v) to pH 7.0–7.5.

2.8 Centrifuge at 2300×g for 15 minutes at room temperature. Separate carefully the supernatant so that it does not get contaminated with the precipitate.

2.9 Ultrafiltrate the supernatant by a 5000 Da molecular cut membrane until approximately ½ its volume. Add water MilliQ to initial volume and ultrafiltrate to ½ its volume. Repeat the process 4 times.

2.10 Examine the concentrated washed supernatant resulting from the previous step by reverse phase column (Vydac C4) chromatography, purifying the polypeptide that eludes with a concentration of acetonitrile between 18 and 22%.

2.11 Evaporate the solvent by lyophilization and eliminate the excess salts by diafiltration or chromatography in BioGel P10 or similar.

2.12 It can be lyophilized if so desired.

2.13 By means of this process a pure product is obtained in quantities ranging from 0.2 and 1.0 g polypeptide/100 g seed of R. communis, which allows for its industrial scaling.

The polypeptide thus obtained has a molecular weight of 12 KDa±0.5 KDa, determined by mass spectroscopy, it is dimeric, as determined by polyacrylamide gel electrophoresis denaturating and reducing conditions (H Schagger, G von Jagow "Tricine-sodium dodecyl sulfate polyacrylamide gel electrophoresis for the separation of proteins in the range from 1 to 100 KDa" Anal. Biochem. 166,368–379 (1987)), the dimers being united by disulphur bridges as can be deduced from the need to use reducing conditions for the resolution by electrophoresis; it is resistant to trypsin (incubated for 24 hours at 37° C. in 0.1 M Tris-HCl pH 8.5 in a polypeptide protease ratio 30:1), pepsine (incubated 24 hours at 37° C. in 0.01 M HCl in a polypeptide protease ratio 25:1) and complies with the rest of the requirements described in the General Specifications of the Invention. Its sequence, determined by Edman degradation, is as follows:

Minor subunit:
ESKGEREGSSSQQCRQEVQRKDLSSCERYLRQSSSRR
(SEQ ID NO:2)

Major subunit:
QQQESQQLQQCCNQVKQVRDECQCEAIKYIAEDQIQQGQLHGEESERVAQ RAGEIVSSCGVRCMRQTR
(SEQ ID NO:3)
(the amino acids specified in the censensus sequence are indicated by boldface)

The polypeptide thus obtained induces per se the proliferation of the splenic cells with a maximum proliferation index with a value of 5 at a concentration of 3 μg/ml.

3. Formation of the Conjugate.

Starting from the polysaccharide, obtained as indicated in point 1 of this example, dissolved in water at a concentration of 1 mg/ml, in a total volume of 50 ml, and of the polypeptide, obtained as indicated in point 2 of this example, dissolved in water at a concentration of 1 mg/ml, in a total volume of 10 ml. Pour into a glass at room temperature 34 ml of the polysaccharide solution and 6.5 ml of the polypeptide solution and add water to a final volume of 300 ml, incorporate a magnet and shake at 50 rpm for 30 minutes. After this time, extract 1 ml aliquots and keep frozen until its administration to the experimental animals.

4. Biological Activity: Inhibition of the Tumor Necrosis Factor (TNF) Production Induced by Bacterial Endotoxin (LPS) in BalB/C Mice Serum The polysaccharide-polypeptide conjugate is administered to Balb/c mice by oral route in a volume of 0.5 ml of a solution prepared as described in point 3 for six consecutive days prior to the intravenous injection of 25 μg per animal of *E coli* endotoxin serotype 055:B5. The result obtained with this treatment is an inhibition of 65% in the TNF serum levels obtained 90 minutes after LPS administration.

None of the two components of the polysaccharide-polypeptide conjugate administered individually at doses similar to the ones found in the conjugate show activity in this assay.

The TNF is determined by a bioassay in which the cytotoxicity of the serum versus the L929 cell line is measured (T Mosmann "Rapid colorimetric assay for cellular growth and survival: Application to proliferation and cytoxicity assays" J. Immunol. Methods 65, 55–63 (1983).

EXAMPLE 2

1. Obtaining the Polysaccharide

Starting from *C. utilis*, as described in Example 1, section 1.

2. Obtaining the Polypeptide

It is obtained, for example, based on the processes described by F S Sharief, S S L Li "Aminoacid sequence of a small and large subunits protein from *Ricinus communis*" J. Biol. Chem. 257, 14753–14759 (1982); J Godinho da Silva Jr, O L T Machado, C Izumi, J C Padovan, B T Chait, U A Mirzaa, L J Geene "Aminoacid sequence of a new 2S albumin which is part of a 29-kDa precursor protein" Arch. Biochem. Biophys. 336, 10–18 (1996); G M Neumann, R. Condron, G M Polya "Purification and sequencing of napin-like protein small and large subunits from *Momordica charantia* and *Ricinus communis* seeds and determination of sites phosphorylated by plant $Ca^{2+}$ dependent protein kinase" Biochem. Biophys. Acta 1298, 223–240 (1996); M E H Bashir, I Hubatsch, H P Leinenbach, M Zeppezauer, R C Panzani, I H Hussein "Ric c 1 and Ric c 3, the allergenic 2S albumin storage proteins of *Ricinus communis:* Complete primary structures and phylogenetic relationships" Int. Arch. Allergy Immunol. 115, 73–82 (1998), in the following way:

In this example, the polypeptide, an integral part of the conjugate object of the present invention, is obtained starting from non-germinated seeds of *Ricinus communis*, by the method described below:

2.1 Grind 100 g of whole seeds, previously washed in water, until a non compact paste is obtained.

2.2 The obtention of the extract is carried out by magnetic stirring the paste with 500 ml of water for 18 hours at 4° C.

2.3 Next, eliminate the residue of the seeds by successive filtration through a stainless steel filter mesh of 0.2 mm light, Hyflo supercell coating, and by prefilter of polypropylene and filters of nitrocellulose or similar with 40 mm diameter and light of 80 ìm, 8 ìm, 5 ìm, 0.45 ìm and 0.22 ìm 2.4 The filtrate is acidified to pH 1.5 with phosphoric acid diluted with water MilliQ at 50% (v/v).

2.5 Heat at 56° C. in a water-bath with thermostat for 120 minutes with gentle magnetic stirring.

2.6 Centrifuge at 2300× g for 15 minutes at room temperature. Separate carefully the supernatant so that it does not get contaminated with the precipitate.
2.7 Neutralize the supernatant with a solution of NaOH at 20% (w/v) to pH 7.0–7.5.
2.8 Centrifuge at 2300× g for 15 minutes at room temperature. Separate carefully the supernatant so that it does not get contaminated with the precipitate.
2.9 Ultrafiltrate the supernatant by a 5000 Da molecular cut membrane to approximately ½ its volume. Add water MilliQ to initial volume and ultrafiltrate to ½ its volume. Repeat the process 4 times.
2.10 Examine the concentrated washed supernatant resulting from the previous step by reverse phase column (Vydac C4) chromatography, purifying the polypeptide that eludes with a concentration of acetonitrile between 22 and 24%.
2.11 Evaporate the solvent by lyophilization and eliminate the excess salts by diafiltration or chromatography in BioGel P10 or similar.
2.12 It can be lyophilized if so desired.
2.13 By means of this process a pure product is obtained in quantities ranging from 0.2 and 1.0 g polypeptide/100 g seed of *R. communis*, which allows for its industrial scaling.

The polypeptide thus obtained has a molecular weight of 11 KDa±0.5 KDa, determined by mass spectroscopy, it is dimeric, as determined by polyacrylamide gel electrophoresis under denaturating and reducing conditions (H Schagger, G von Jagow "Tricine-sodium dodecyl sulfate polyacrylamide gel electrophoresis for the separation of proteins in the range from 1 to 100 KDa" Anal. Biochem. 166, 368–379 (1987)) the dimers being united by disulphur bridges as can be deduced from the need to use reducing conditions for the resolution by electrophoresis; it is resistant to trypsin (incubated for 24 hours at 37° C. in 0.1 M Tris-HCl pH 8.5 in a polypeptide protease ratio 30:1), pepsine (incubated 24 hours at 37° C. in 0.01M HCl in a polypeptide protease ratio 25:1) and complies with the rest of the requirements described in the General Specifications of the Invention. Its sequence, determined by Edman degradation is as follows:

```
Minor subunit:
PSQQGCRGQIQEQQNLRQCQEYIKQQVSGQGPRR
(SEQ ID NO:4)

Major subunit:
QERSLRGCCDHLKQMQSQCRCEGLRQAIEQQQSQGQLQGQDVFEAFRTAA

NLPSMCGVSPTECRF
(SEQ ID NO:5)
(the amino acids specified in the consensus
sequence are indicated by boldface)
```

The polypeptide thus obtained induces per se the proliferation of the splenic cells with a maximum proliferation index with a value of 4 at a concentration of 6 μg/ml.

3. Formation of the Conjugate.

Starting from the polysaccharide, obtained as indicated in point 1 of example 1, dissolved in water at a concentration of 1 mg/ml, in a total volume of 50 ml. Starting from the polypeptide, obtained as indicated in point 2 of this example, dissolved in water at a concentration of 1 mg/ml, in a total volume of 10 ml. Pour into a glass at room temperature 34 ml of the polysaccharide solution and 6.5 ml of the polypeptide solution and add water to a final volume of 300 ml, incorporate a magnet and stir at 50 rpm for 30 minutes. After this time, extract the 1 ml aliquots and keep frozen until its administration to the experimental animals.

4. Biological Activity: Inhibition of the Tumor Necrosis Factor (TNF) Production Induced by Bacterial Endotoxin (LPS) in BalB/C Mice Serum The polysaccharide-polypeptide conjugate is administered to Balb/c mice by oral route in a volume of 0.5 ml of a solution prepared as described in point 3 for six consecutive days prior to the intravenous injection of 25 μg per animal of *E coli* endotoxin serotype 055:B5. The result obtained with this treatment is an inhibition of 55% in the TNF serum levels obtained 90 minutes after LPS administration.

None of the two components of the polysaccharide-polypeptide conjugate administered individually at doses similar to the ones found in the conjugate show activity in this assay.

The TNF is determined by a bioassay in which the cytotoxicity of the serum versus the L929 cell line is measured (T Mosmann "Rapid colorimetric assay for cellular growth and survival: Application to proliferation and cytoxicity assays" J. Immunol. Methods 65, 55–63 (1983).

EXAMPLE 3

1. Obtaining the Polysaccharide

Starting from *C. utilis* as described in Example 1, section 1.

2. Obtaining the Polypeptidess

It is obtained, for example, based on the process described by F S Sharief, S S L Li "Aminoacid sequence of a small and large subunits protein from *Ricinus communis*" J. Biol. Chem. 257, 14753–14759 (1982); J Godinho da Silva Jr, O L T Machado, C Izumi, J C Padovan, B T Chait, U A Mirzaa, L J Geene "Aminoacid sequence of a new 2S albumin which is part of a 29-kDa precursor protein" Arch. Biochem. Biophys. 336, 10–18 (1996); G M Neumann, R. Condron, G M Polya "Purification and sequencing of napin-like protein small and large subunits from *Momordica charantia* and *Ricinus communis* seeds and determination of sites phosphorylated by plant $Ca^{2+}$ dependent protein kinase" Biochem. Biophys. Acta 1298, 223–240 (1996); M E H Bashir, I Hubatsch, H P Leinenbach, M Zeppezauer, R C Panzani, I H Hussein "Ric c 1 and Ric c 3, the allergenic 2S albumin storage proteins of *Ricinus Communis*: Complete primary structures and phylogenetic relationships" Int. Arch. Allergy Immunol. 115, 73–82 (1998), in the following way:

In this example, the polypeptides, an integral part of the conjugate object of the present invention, are obtained starting from non-germinated seeds of *Ricinus communis*, by the method described below:

2.1 Grind 100 g whole seeds, previously washed in water, until a non compact paste is obtained.

2.2 The obtention of the extract is carried out by magnetic stirring the paste with 500 ml of water for 18 hours at 4° C.

2.3 Next, eliminate the residue of the seeds by successive filtration through a stainless steel filter mesh of 0.2 mm light, Hyflo supercell coating, and by prefilter of polypropylene and filters of nitrocellulose or similar with 40 mm diameter and light of 80 ìm, 8 ìm, 5 ìm, 0.45 ìm and 0.22 ìm 2.4 The filtrate is acidified to pH 1.5 with phosphoric acid diluted with water MilliQ at 50% (v/v).

2.5 Heat at 56° C. in a water bath with thermostat for 120 minutes with gentle magnetic stirring.

2.6 Centrifuge at 2300× g for 15 minutes at room temperature. Separate carefully the supernatant so that it does not get contaminated with the precipitate.

2.7 Neutralize the supernatant with a solution of NaOH at 20% (w/v) to pH 7.0–7.5.

2.8 Centrifuge at 2300× g for 15 minutes at room temperature. Separate carefully the supernatant so that it does not get contaminated with the precipitate.

2.9 Ultrafiltrate the supernatant by a 5000 Da molecular cut membrane to approximately ½ its volume. Add water MilliQ to initial volume and ultrafiltrate to ½ its volume. Repeat the process 4 times.

2.10 Next it is purified by molecular permeation chromatography in BioGel P10, pass over the area, with an elution volume below the total, which gives positive for the Lowry reaction (O H Lowry, H J Rosenbrough, A L Farr, R J Randall "Protein measurement with the Folin phenol reagent." J. Biol. Chem. 193,265–275 (1951)) and disregard the eluate at a volume equal or greater than the total layer.

2.11 It can be lyophilized if so desired.

2.12 By means of this process a mixture of the two polypeptides previously described (examples 1 and 2), in ratios polypeptide 1/polypeptide 2 in the range of 35/75 to 75/35 and in quantities in the range of 0.4 and 1.2 g of both polypeptides/ 100 g seeds of *R. communis*, which allows for its industrial scaling.

The polypeptides thus obtained induce per se, when administered jointly in the ratio obtained (2/1 12 kDa polypeptide/11 kDa polypeptide) the proliferation of the splenic cells with a maximum proliferation index with a value of 6 at a concentration of 3 μg/ml.

3. Formation of the Conjugate.

Starting from the polysaccharide, obtained as indicated in point 1 of example 1, dissolved in water at a concentration of 3.75 mg/ml, in a total volume of 150 ml. Start from the polypeptides, obtained as indicated in point 2 of this example, dissolved in water at a concentration of 0.75 mg/ml, in a total volume of 150 ml. Pour into a glass at room temperature both solutions, incorporate a magnet and stir at 50 rpm for 30 minutes. After this time, freeze, lyophilize and keep it frozen until it is administered to the experimental animals, at which time it is dissolved in distilled water at an adequate concentration for the required dose.

The infrared spectrum of the glycoconjugate thus obtained is shown in FIG. 1. This spectrum has been carried out in a potassium bromide pellet, with a concentration of the glycoconjugate of 0.2%, in an infrared spectrophotometer Perkin-Elmer model 881, passing through 4000 to 600 $cm^{-1}$ in 6 minutes with variable slot, resolution at 1000 $cm^{-1}$ and spectral noise of 0.5% T and adjusted electronically by a Savitzky/Golay process and automatically expanded in absorbance.

4. Biological Activity:

Inhibition of the Tumor Necrosis Factor (TNF) Production Induced by Bacterial Endotoxin (LPS) in BalB/C Mice Serum The polysaccharide-polypeptide conjugate is administered to Balb/c mice by oral route in a volume of 0.5 ml at a dose of 3 mg/Kg for six consecutive days prior to the intravenous injection of 25 μg per animal of *E coli* endotoxin serotype 055:B5. The result obtained with this treatment is an inhibition of 65% in the TNF serum levels obtained 90 minutes after LPS administration.

The TNF is determined by a bioassay in which the cytotoxicity of the serum versus the L929 cell line is measured (T Mosmann "Rapid colorimetric assay for cellular growth and survival: Application to proliferation and cytoxicity assays" J. Immunol. Methods 65, 55–63 (1983).

Effect of Multiple Doses of the Polysaccharide-Polypeptides Conjugate on the Production of TNF Induced by Serum in Mice.

Multiple doses of the conjugate were administered to mice with the same treatment schedule previously described. The result indicates that there is a dose-effect relationship between the inhibition of TNF and the dose of the conjugate. The dose-effect curve presents a bell shape reaching a maximum inhibition of 90% at a dose of 48 mg/Kg.

Increase of the Hematopoietic Activity Evaluated by the Increase in the Number of Precursor Cells in the Granulocyte-macrophage Line (CFU-GM).

The intravenous administration of a single dose of 2 mg/kg in a volume of 0.25 ml of the polysaccharide-polypeptide conjugate to mice C57BI/6 induces the formation of precursor cells in the granulocyte-macrophage line measured five days after administration.

The intravenous administration of the polypeptides at doses similar to that shown in the conjugate produce an increase of 227% in the number of precursor cells CFU-GM. The individual administration by intravenous route of the polysaccharide at doses equivalent to that found in the conjugate did not have any effect in this assay. When the conjugate is administered at the dose previously described the activity increases up to 3763%.

Increase in Survival of Mice Infected with *Listeria Monocytogenes* and Immunosuppressed.

The administration of 3 mg/Kg of the conjugate at a volume of 0.5 ml, by oral route, to Swiss mice for six consecutive days prior to the infection produce a protection in mice immunosuppressed with silica and infected with *L. monocytogenes*. Immunosuppression is induced by treatment with 120 mg/kg of silica administered intraperitoneally one day before causing the infection. The protection manifested itself as an increase in the lethal dose 50, which in animals treated with the conjugate reached a value similar to that in non-immunosuppressed animals.

Restoration of the Antitumoral Cytotoxic Activity of NK Cells in Immunocompromised Animals The treatment with 3 mg/kg of conjugate in a volume of 0.5 ml, for four consecutive days increases the NK activity in splenic cells of normal mice and normalizes it if it is diminished, as occurs in the case of old mice and immunosuppressed mice with cyclophosphamide at a single dose of 180 mg/kg.

Effect on the Macrophage Function in Mice

The conjugate administered in a volume of 0.2 ml at a dose of 0.9 mg/kg to Balb/c mice by oral route for six consecutive days increase the phagocytic and bactericide capacity of peritoneal macrophages against *Staphilococcus aureus* with a clear relationship between the duration of treatment and the response levels observed.

When macrophages fight the intracellular pathogen *Candida guillermondi*, an increase is observed in the phagocytary values as well as in the microbicide capacity.

Activity on Pulmonary Edema Induced by Intranasal Endotoxin

A pulmonary edema was induced by instillation of 400 ìg of LPS of *E. coli* 0.55:B5 of Sigma, evaluating the edema by visual inspection of the pulmonary surface 3 days after administration. The daily intraperitoneal administration of the conjugate at various doses (in the range 0.9 to 4.5 mg/kg) in 0.5 ml of apyrogenous sterile water from the day of LPS administration until the sacrifice of the animal, produces a clear decrease in the edema, with an effective dose 50 of 1.67 mg/kg.

Acute Toxicity Assay in Mice

The oral administration to mice of CD1 strain of a 200 mg/kg dose in 1 ml of polysaccharide-polypeptides conjugate did not prove toxic since it did not cause mortality or alterations in corporal weight, nor in the macro or microscopic weight and aspect of the main vital organs.

Activity on Metabolization Processes at Hepatic Level

The conjugate administered by oral route at a dose of 3 mg/kg in 0.5 ml, to Sprague-Dowley rats, does not interfere with the clearance of antipyrin. Administered in a single dose three times greater in 0.5 ml by oral route to rats of the same strain during six consecutive days does not modify the contents of cytochrome P450, cytochrome b5 and NADPH cytochrome c reductase, nor does it modify the biotransformation enzymatic activities related to cytochrome P450 (Phase I), nor to phase II conjugate enzymes of phase II in hepatic microsomes of rats.

The invention claimed is:

1. A glycoconjugate formed by non-covalent association of a polysaccharide with a polypeptide, wherein the polysaccharide has a molecular weight of 150 KDa±30 KDa, one phosphate group per 15 monosaccharide residues, with 84±6% of mannose, 7±3% glucose and 1±1% galactose making up a main skeleton integrated by 1–6 bonds with 1–2 branches; wherein the polypeptide comprises a minor subunit of SEQ ID NO: 2 or 4 and a major subunit of SEQ ID NO: 3 or 5 with a molecular weight of 11 or 12 Kda; wherein the molar ratio of the polysaccharide to the polypeptide is about 1:2.5, and wherein said glycoconjugate has activity in inhibiting the production of tumor necrosis factor (TNF) in a patient when an effective amount of the glycoconjugate is administered.

2. The glycoconjugate as claimed in claim 1, wherein the polypeptide is stabilized by disulphur bridges, and is oligomeric or dimeric.

3. The glycoconjugate as claimed in claim 1, wherein the polypeptide is stabilized by at least two intercatenary bridges.

4. The glycoconjugate of claim 3, wherein the at least two intercatenary bridges are disulphur bridges.

* * * * *